United States Patent [19]

Collier et al.

[11] Patent Number: 4,738,333

[45] Date of Patent: Apr. 19, 1988

[54] SOBRIETY INTERLOCK WITH UNSUPERVISED CONFIRMATION OF OPERATOR IDENTITY

[75] Inventors: Donald W. Collier, Chicago, Ill.; Kip L. Fuller, Denver, Colo.; Felix J. E. Comeau, Brampton, Canada

[73] Assignee: Guardian Technologies, Inc., Denver, Colo.

[21] Appl. No.: 907,881

[22] Filed: Sep. 16, 1986

[51] Int. Cl.$^4$ .......................... B60R 1/00; G08B 23/00
[52] U.S. Cl. ..................................... 180/272; 340/561; 340/576; 307/10 R; 422/84
[58] Field of Search ......................... 180/272; 423/63; 422/84; 340/52 R, 561, 562, 576; 307/10 R

[56] References Cited

U.S. PATENT DOCUMENTS

| | | | |
|---|---|---|---|
| 3,690,838 | 9/1972 | Luckey | 23/254 R |
| 3,764,274 | 10/1973 | Collier | 23/255 F |
| 3,780,311 | 12/1973 | Brown | 307/10 R |
| 3,809,067 | 5/1974 | Hoppesch | 128/2 C |
| 3,823,601 | 7/1974 | Hoppesch | 73/23 |
| 3,824,537 | 7/1974 | Albertson | 340/53 |
| 3,831,707 | 8/1974 | Takeuchi | 180/99 |
| 4,093,945 | 6/1978 | Collier | 340/279 |
| 4,592,443 | 6/1986 | Simon | 180/272 |
| 4,678,057 | 7/1987 | Elfman et al. | 180/272 |

OTHER PUBLICATIONS

Dr. Robert Breakspere, Development of the Lion Analytics VBM Breath Alcohol Activated Interlock, Sept. 17, 1986.
Dr. Ronald Garren, Paper Presented for Presented for Presentation at the Workshop on In-Vehicle Alcohol Test Devices, Sept. 17, 1986.
Ms. Patricia L. Zajac, Manufacturers Issues, Sept. 17, 1986.

*Primary Examiner*—Richard A. Bertsch
*Attorney, Agent, or Firm*—Wood, Herron & Evans

[57] ABSTRACT

A sobriety interlock system prevents a vehicle or other equipment from being started unless the identity of a designated operator is confirmed by the system and the operator passes a breath sobriety test. The designated operator is trained to perform a physical act, the successful completion of which can be determined by the system and which requires at least a predetermined number, N, of attempts to learn. A necessary precondition for starting the vehicle is satisfied when the system determines that the identity-confirming act has been performed in fewer than N attempts.

64 Claims, 10 Drawing Sheets

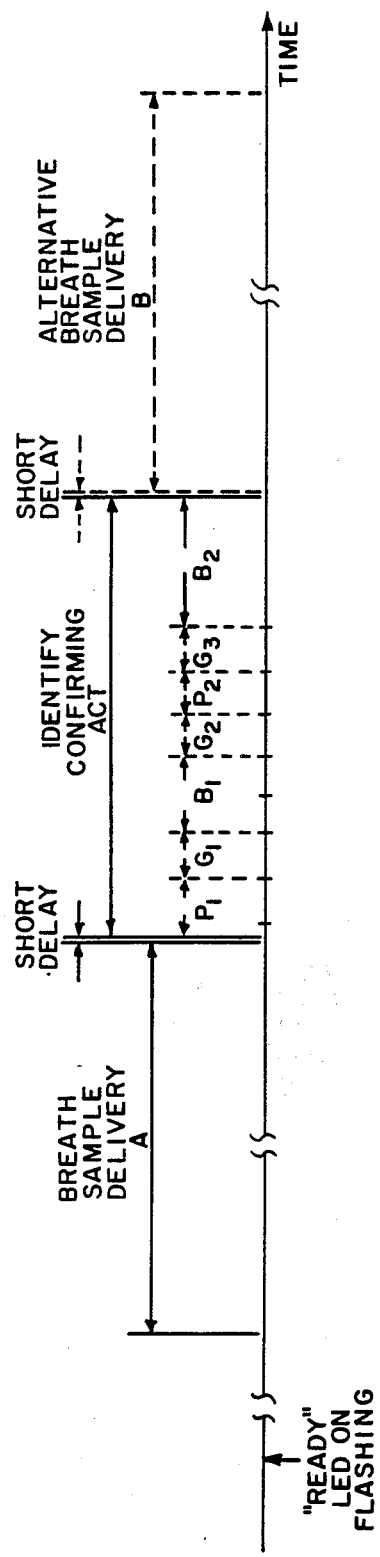

SOBRIETY INTERLOCK WITH UNSUPERVISED CONFIRMATION OF OPERATOR IDENTITY

FIELD OF THE INVENTION

The present invention relates to breath sobriety testing. More particularly, the invention relates to an interlock system operable to enable operation of a vehicle such as an automobile or other equipment based on the alcohol content of the breath of an operator whose identity is confirmed by the system.

BACKGROUND OF THE INVENTION

The operation of vehicles by persons under the influence of alcohol is a major safety problem in the United States and many other countries. Despite growing public awareness and government concern, statistics continue to show that a high percentage of automobile accidents causing serious injury or death involve drivers who have been drinking alcoholic beverages in excess. Injuries in the workplace are also often found to be related to the operation of heavy equipment or other machinery by persons impaired by the effects of alcohol.

To address this problem, various attempts have been made to develop devices which prevent automobiles and the like from being operated by inebriated individuals. Such interlock devices typically operate according to the well known principle that the gas present in the alveoli of the lungs has an alcohol content directly proportional to that of the bloodstream. Blood alcohol content (B.A.C.) thus can be accurately determined by breath testing. A typical breath testing sobriety interlock of this general type is illustrated in U.S. Pat. No. 3,780,311. When breath alcohol measurements are used as the basis of a sobriety interlock, it is, particularly for a vehicle interlock, desirable that the system include anti-defeat means capable of reasonably insuring a correct test result without human super-vision. Such anti-defeat means should preferably satisfy several desiderata.

An unsupervised interlock system must be capable of discriminating between a contemporaneous breath sample and substitute gases such as air from bicycle pump or a filling station air hose, bellows or previously inflated balloon. Illustrations of systems aimed at achieving the foregoing are discussed in U.S. Pat. Nos. 4,592,443, 3,831,707, and 3,824,537. U.S. Pat. No. 4,592,443 proposes measuring the temperature of the gas and determining whether it falls within a range expected for breath. Breath being moist, U.S. Pat. No. 3,831,707 proposes sensing humidity in the gas to avoid circumventing the system with dry gases. U.S. Pat. No. 3,824,537 teaches requiring the operator to place one hand on a button which must be activated during a test period while the other hand is used to hold a breath sampling tube located some distance away from the button. Since both hands of the operator are placed apart, deceptive manipulation of a bellows or the like is discouraged.

Secondly, an unsupervised interlock system must insure that the measurement is based on a sample of alveolar gas, commonly referred to in the art as a "deep lung sample", which term as used herein and in the claims refers to a breath sample consisting of a proportion of alveolar gas sufficient to permit an accurate determination of blood alcohol level. Since breath expired from uper portions of the respiratory tract does not necessarily have an alcohol level porportional to that of the bloodstream, a deep lung sample is essential if the system is not to be defeated by shallow exhalations or a series of short puffs of breath expelled from upper portions of the respiratory tract. This problem is addressed effectively in U.S. Pat. Nos. 4,093,945 and 3,764,270 issued to Collier et al. The Collier et al. patents disclose means, preferably a pressure switch and timer system, to insure an essentially continuous and uninterrupted flow of breath sufficient to yield a deep lung sample.

A third important requirement in an unsupervised interlock system which has not been addressed by the prior art is the need for effectively deterring a person other than a designated prospective vehicle operator from taking the breath test in place of that operator in order to start the vehicle. A system for confirming the identity of the operator is particularly needed in sobriety interlocks for use in situations where use of the interlock by the operator is not entirely voluntary so that the likelihood of attempts to defeat the interlock are increased. One example of such a situation is where an employer seeks liability protection by installing interlocks on vehicles operated by employees. Another example is in the court-supervised rehabilitation of offenders found to have been driving while under the influence of alcohol (DUI).

As a condition for permitting a DUI offender to drive in order to maintain employment and/or obtain counselling, some courts may require a sobriety interlock to be installed in the offender's car. To protect the safety of both the offender and the public to the fullest extent possible, reasonable assurance must be provided that others will not be able to substitute themselves for the DUI offender in the alcohol breath test procedure should the latter become intoxicated and, having successfully passed the test, then start the car for the DUI offender.

Accordingly, there exists a need for a sobriety interlock system capable of discriminating without human supervision, between a designated vehicle operator and other persons to prevent circumvention of the system. Further, there is a need for such a sobriety interlock system which provides for insuring that interlocked equipment can be stated only after the designated operator passes a breath sobriety test which is based on a contemporaneous deep lung sample of breath.

SUMMARY OF THE INVENTION

The present invention satisfies the above needs by providing a sobriety interlock apparatus and method which, without requiring human supervision, confirms the identity of a designated driver of the vehicle to effectively deter persons other than a designated driver from successfully taking the sobriety test in order to allow the vehicle to be started and thereafter driven by a designated driver who may be inebriated. The system also requires the sobriety test to be based on a deep lung sample of breath to assure a valid test.

According to the invention, a designated driver of the vehicle is trained to perform an identity-confirming physical act which cannot be readily learned by most persons without practicing the identity-confirming act at least a predetermined minimum number of times. Upon sensing successful completion of the act within fewer attempts than the predetermined minimum number of tries required by most persons to initially learn the act, the identity of the designated driver is confirmed, thereby satisfying a necessary precondition for starting the vehicle. While any act satisfying the above requirements may serve as an identity-confirming act, the confirming act preferably requires placing the mouth or lips over the breath sample delivery port of the interlock system. By requiring use of the same physical location to both perform the confirming act and deliver a breath sample for breath alcohol analysis purposes, further assurance is provided that these two acts will not be performed by different persons.

In some preferred embodiments of the invention, driver identity confirmation is actually performed before or after a breath sample is delivered for blood alcohol content determination. However, if the confirming act is separated in time from the time of delivery of the breath sample, the time interval of separation should be too brief to permit more than one person to effectively participate in the test. In other words, the delay, if any, between the confirming act and delivery of a breath sample must be a time interval too brief to permit the confirming act and the breath sample to be provided by different individuals. A deep lung breath sample is assured by requiring delivery of an essentially continuous, uninterrupted flow of breath for at least 4 seconds.

In other preferred embodiments of the invention, further assurance that the person delivering a breath sample is the same person performing the identity-confirming act by at least partially temporarily overlapping the confirming act with delivery of the breath sample.

BRIEF DESCRIPTION OF THE DRAWINGS

FIG. 3 is a timing diagram illustrating a preferred identity-confirming act and showing its relationship to breath sample delivery.

FIGS. 4A-4F are a series of flowcharts illustrating the operation of the system of FIG. 1 wherein:

FIG. 4A illustrates the INT routine;
FIG. 4B illustrates the READY routine;
FIG. 4C illustrates the BLOW routine;
FIG. 4D illustrates the BLOCMP routine;
FIG. 4E illustrates the PASS routine; and
FIG. 4F illustrates the ID routine.

DETAILED DESCRIPTION OF THE INVENTION

Figure 1:
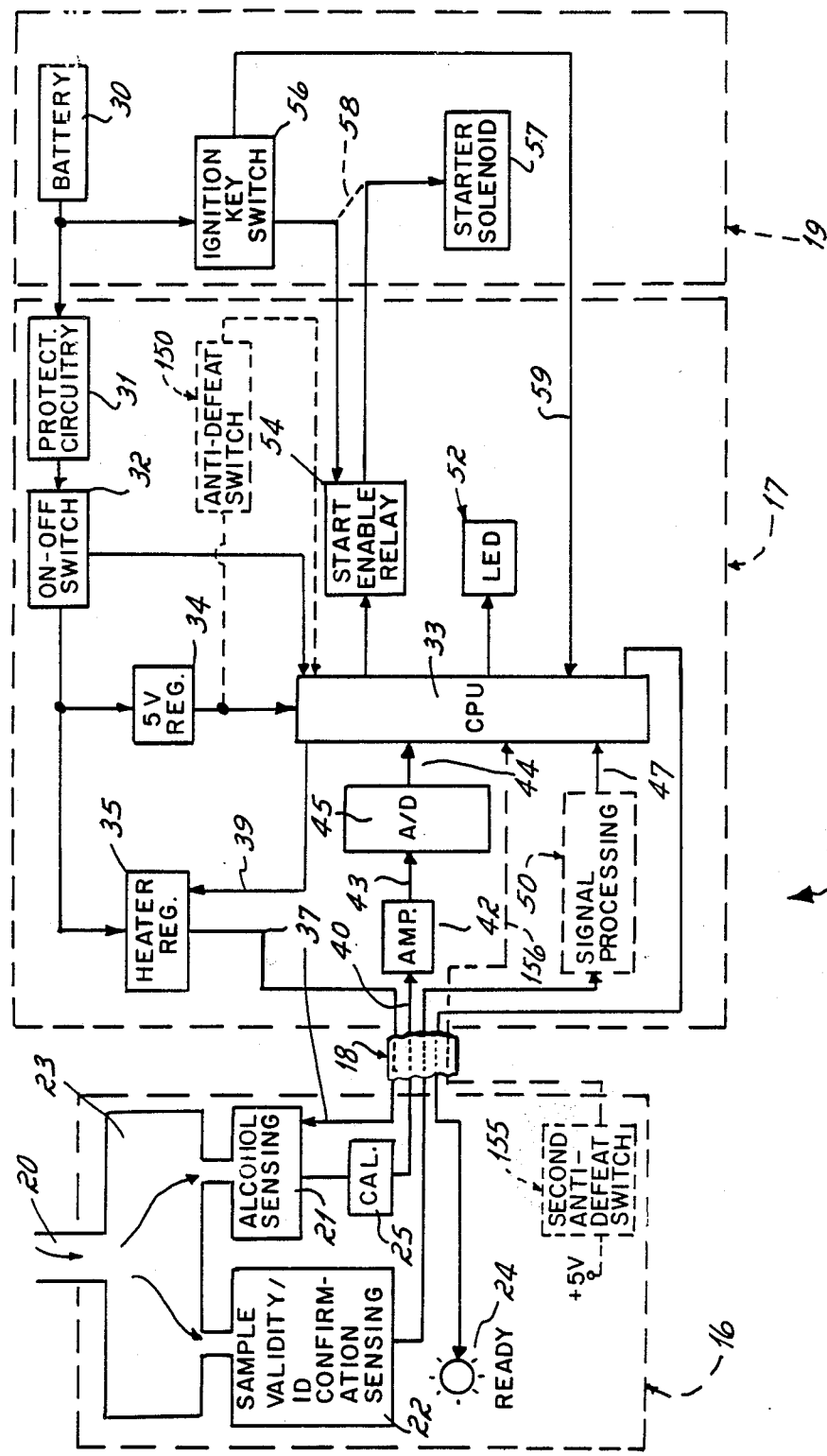
FIG. 1 is a block diagram of a sobriety interlock system embodying the present invention shown connected to a vehicle ignition system.

Referring to FIG. 1, a sobriety interlock 15 embodying the invention includes a remote sampling head 16 connected to a main control module 17 by way of a detachable cable 18. Interlock 15 is connected to a vehicle ignition system 19 in order to prevent the vehicle from being started unless a designated driver whose identity is confirmed by the system passes a breath sobriety test upon delivering a deep lung sample of breath to sampling head 16. Control module 17 is preferably mounted under the dashboard of the vehicle while control cable 18 is of sufficient length of permit sampling head 16 to be removeably fastened to the front or top surface of the dashboard by Velcro or other means in a position readily accessible from the driver's seat. Sampling head 16 includes a breath inlet port 20 which communicates via a manifold 23 with an alcohol sensing device 21 and sample validity/identity confirmation sensing means 22. Sampling head 16 also includes a "Ready" LED 24 to indicate when the interlock 15 is ready to receive or is in the process of receiving a breath sample. Also contained within sampling head 16 is a calibration potentiometer 25 for calibrating the response of interlock 15 to a particular concentration of alcohol. By detaching cable 18, sampling head 16 is readily disconnected from control module 17 so that sampling head 16 can be removed for replacement, repair or calibration without the necessity of removing control module 17 from the vehicle.

Sobriety interlock 15 is supplied power from vehicle battery 30 through protection circuitry 31 and momentary contact on-off switch 32 which is mounted in a location on the surface of control module 17 accessible to the operator. Switch 32 communicates with a central processing unit (C.P.U) 33 which is supplied power from a 5 volt regulator 34 connected to the load side of switch 32. C.P.U. 33 disables vehicle starter solenoid 57 whenever switch 32 is turned off or whenever power is otherwise removed from C.P.U. 33. Switch 32 also supplies power from battery 30 to a low-voltage heater regulator 35 which supplies a variable duty cycle voltage signal 37 to alcohol sensing device 21. The duty cycle of signal 37 is controlled according to the duty cycle of a signal 39 emanating from C.P.U. 33. Alcohol sensing device 21 generates an alcohol sensor signal 40 which is correlated to the alcohol concentration in the breath sample received by device 21 through breath inlet port 20. Alcohol sensor signal 40 is amplified by an amplifier 42, to yield alcohol level signal 43 which is converted to a digital blood alcohol concentration (B.A.C.) signal 44 by analog to digital (A/D) converter 45. C.P.U. 33 also receives one or more smple validity/identity confirmation signals 47 emanating from sample validity/identity confirmation sensing means 22 by way of signal processing means 50. Provided that signal 47 indicates to C.P.U. 33 that the breath sample is value (i.e., it is a deep lung sample), and the identity of the operator is confirmed, C.P.U. 33 lights an appropriate one of a group of LED's 52 and, if the test has been passed, enables starting of the vehicle by energizing a start enable relay 54 which has been wired between ignition key switch 56 and starter solenoid 57. Interlock 15 is installed in the vehicle by connecting protection circuitry 31 to battery 30 and connecting ignition key switch 56 with starter solenoid 57 through a normally open contact of start enable relay 54 after disconnecting line 58 which ordinarily connects key switch 56 with solenoid 57. Ignition key switch 56 is also connected to C.P.U. 33 by way of wire 59 which is energized whenever vehicle ignition switch 56 is in the start or run position.

FIRST PREFERRED EMBODIMENT

Figure 2:
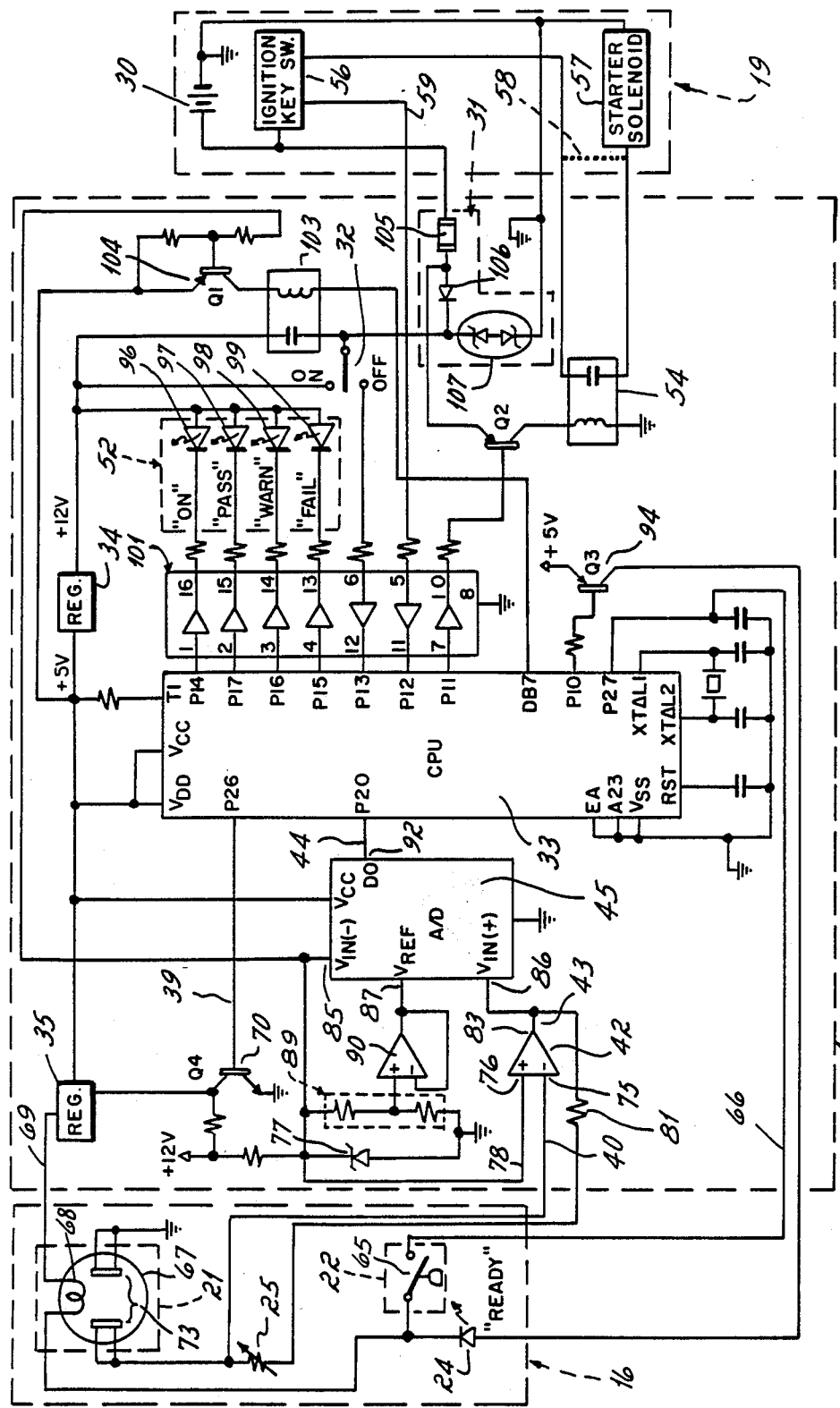
FIG. 2 is an electrical schematic illustrating a first preferred embodiment of a sobriety interlock system of the type shown in FIG. 1.

A first preferred embodiment of the sobriety interlock system of FIG. 1 is shown in detail in FIG. 2 wherein like reference numerals designate like items. In the first preferred embodiment, sample validity/identity confirmation sensing means 22 is a pressure switch 65, such as Fairchild model PSF 100A-3.0, connected to manifold 23 as to respond to the flow of breath through inlet port 20. The state of pressure switch 65 is sensed by C.P.U. 33 at pin P27 by way of line 66. C.P.U. 33 is preferably an Intel Co. part No. 8748 HMOS-E single-component 8-bit microcomputer. Alcohol sensing device 21 may consist of a semiconductor sensor which is preferably model TGS #812 manufactured by Figaro Engineering Company. Alternatively, sensing device 21 may consist of a Model TGS #813, also manufactured by Figaro Engineering Company. Sensor 67 includes a heater 68 which can be energized by way of line 69 by a low voltage heater regulator 35 which is preferably a Texas Instruments type TL497ACN switching voltage regulator. The power delivered to heater 68 is controlled by C.P.U. 33 by outputting an adjustable duty cycle signal 39 from pin 26 to transistor Q4 70 which communicates with regulator 35 by way of line 71 to vary the duty cycle of the output signal of regulator 35 appearing on line 69. Sensor 66 also includes an alcohol sensing element 73. The resistance of element 73 changes in accordance with the alcohol concentration of the breath sample delivered to inlet port 20 to generate alcohol sensor signal 40 received at the inverting input 75 of amplifier 42 which generates alcohol level signal 43. Amplifier 42 is an operational amplifier (OP AMP) whose noninverting input 76 receives a temperature compensated reference voltage from a reference diode 77 by way of line 78. Reference diode 77 is preferably a National Semiconductor type LM336Z-25. The gain of OP AMP 42 is determined by a fixed resistor 81 connected in series with calibration potentiometer 25 between the output 83 of amplifier 42 and its inverting input 75. It can be appreciated that fixed resistor 81 and calibration potentiometer 25 can be viewed as a single resistance connected in a voltage dividing relationship with the varying resistance of alcohol sensing element 73. Since OP AMP 42 will tend to maintain the voltage across terminals 75 and 76 at a fixed value and the voltage at noninverting input 76 is held fixed by diode 77, the current through calibration potentiometer and resistor 81 will vary as sensing element 73 varies in resistance with changes in alcohol concentration. Accordingly, the voltage at the output 83 of OP AMP 42 will vary thereby giving rise to alcohol level signal 43.

The output 83 of OP AMP 42 is connected to the Vin(+) input 86 of A/D converter 45. A/D converter 45 is preferably part number ADC0831 manufactured by National Semiconductor. The Vin(−) input 85 of A/D converter 45 is connected directly to the reference voltage emanating from reference diode 77 while the reference input, Vref 87 of A/D converter 45 receives a fraction of the diode 77 reference voltage by way of voltage divider network 89 and a second amplifier 90.

A/D 45 outputs B.A.C. signal 44 from its data out (DO) port to C.P.U. 33 at pin P20. Pin P10 of C.P.U. 33 is connected by way of transistor Q3 94 with "Ready" LED 24. When the interlock 15 is ready to receive a breath sample, C.P.U. 33 causes "Ready" LED 24 to flash. Once pressure switch 65 closes, indicating a breath sample is being received, "Ready" LED 24 stops flashing and remains lighted steadily until pressure switch 65 opens or the validity time is over, whichever occurs first. "Ready" LED 24 is then turned off until the interlock 15 is again prepared to receive a breath sample. LED's 52 comprise an "ON" LED 96, a "PASS" LED 97, a "WARN" LED 98, and a "FAIL" LED 99 each of which is driven under the control of C.P.U. 33 by way of transistor array 101 which is preferably a Sprague type ULN-2003 high-voltage, high-current Darlington transistor array.

Interlock 15 is energized by moving momentary contact switch 32 is to the "ON" position to supply power from battery 30 is to C.P.U. 33 through 5 volt regulator 34. C.P.U. 33 then generates an output signal at pin DB7 to energize a normally open switch relay 103 by way of transistor Q1 104 to latch the power on. "ON" LED 96 remains lighted by C.P.U. 33 by way of pin P14 through transistor array 101 at all times while power is applied to interlock 15. Interlock 15 is turned off by moving switch 32 to its off position to supply a signal to C.P.U. 33 at pin P13 through transistor array 101 effective to cause C.P.U. 33 to deenergize switch relay 103 thereby deenergizing the system.

The line side of switch 32 is supplied power from battery 30 through protection circuitry 31. Protection circuitry 31 includes a fuse 105 for overcurrent protection, a diode 106 for reverse voltage protection and a bipolar clamp 107 for over-voltage protection.

The first preferred embodiment of the invention may be further understood with reference to the timing diagram of FIG. 3. An operator whose identity is to be confirmed by the interlock 15 is trained to perform an identity-confirming act which preferably involves palcing the mouth or lips over the breath sample delivery port 20. The confirming act should be relatively simple yet, it must be sufficiently difficult to master that is cannot be learned by most persons in less than a given number, N of tries at performing the act. Once learned, the confirming act should be relatively easy for a normal person to remember and perform. However, the degree of difficulty may be raised as required to provide correspondingly increased assurance of proper identification. Otherwise, the precise nature of the conforming act is substantially a matter of choice.

A suitable confirming act is depicted in FIG. 3. It consists of flowing two bursts of breath $B_1$ and $B_2$ of specified duration, each burst of breath being preceded by a pause, $P_1$ and $P_2$, repectively, also of specified duration. The sequence of events the operator must perform is:

Pause ($P_1$), Blow ($B_1$), Pause ($P_1$) and Blow ($B_2$). Preferably, $B_1$ and $B_2$ are each about 1 second. $P_1$ and $P_2$ are about 0.5 seconds each. Alternatively, the identity-confirming act can be modified slightly by not requiring the second burst of breath, $B_2$, to extend for a specified duration. In such case, the identity-confirming act would be successfully completed as soon as C.P.U. 33 senses the beginning of the second burst of breath, $B_2$, occurring after the successful completion of pause $P_2$ at or before the conclusion of grace period $G_3$. Blows $B_1$ and $B_2$ are delivered into sample delivery port 20 with sufficient pressure to cause pressure switch 65 to close while the flow of breath during pauses must be sufficiently small to allow pressure switch 65 to open. By sensing the status of pressure switch 65, by way of line 66, C.P.U. 33 determines whether the sequence of duration of pauses and blows conforms to a representation of the confirming act stored in the memory of C.P.U. 33. If the confirming act is performed successfully, C.P.U. 33 determines that a necessary condition for permitting vehicle starter solenoid 57 to be energized has been satisfied.

Since precise consistency in performance of the confirming act cannot be expected, the invention contemplates the use of one or more "grace periods" which term as used herein and in the claims refers to tolerance intervals adjacent required phases of the confirming act. For example in FIG. 3, blow $B_1$ and $B_2$ are preceded by grace periods $G_1$ and $G_2$ respectively while pause $P_2$ is preceded by grace period $G_2$. While C.P.U. 33 requires pressure switch 65 to be closed for the entire duration of each blow $B_1$, $B_2$ and open for the entire duration of each pause $P_1$, $P_2$, C.P.U. disregards the state of pressure switch 65 during grace periods $G_1$, $G_2$ and $G_3$. In this way, the conforming act can be provided with tolerances so that extreme precision is not required in order to perform the confirming act successfully. In the example of the confirming act depicted in FIG. 3, each grace period is preferably about 0.5 seconds.

In addition to the identity-confirming sensing function, pressure switch 65 also serves to insure a "valid" sample of breath, which term as used herein and in the claims refers to a breath sample delivered in an essentially continuous uninterrupted flow of breath sufficient to yield a deep lung sample. This is accomplished by selecting the switching pressure of switch 65 and the time pressure switch 65 is required to be closed during sample delivery (a period referred to herein as the "validity time") in accordance with the resistance to the flow of breath through the inlet port 20 as to insure a deep lung sample. Since pressure switch 65 must remain closed during breath sample delivery to insure a continuous flow of breath, the identity-confirming act in this embodiment must take place at least partially before or after the confirming act as in intervals A or B of FIG. 3. If, as shown in FIG. 3, breath sample delivery does not overlap the beginning or end portions of the confirming act, the delay interval, if any, between the confirming act and delivery of the breath sample should be too short to permit sampling head 16 to be passed from one person to another. Alternatively, delivery of a breath sample can be timed to overlap at least a portion of the confirming act. This could be accomplished, for example, by requiring breath sample delivery to terminate within a prescribed time limit of its commencement to complete at least the beginning portion of the identity-confirming act. By so temporally overlapping the identity-confirming act with the validity period, further assurance is provided that a single person must perform the act the deliver the sample.

The operation of the embodiment shown in FIG. 2 can be still further understood with reference to the flowcharts of FIGS. 4A through 4F which together illustrate the operation of the software program stored in the memory of C.P.U. 33.

Figure 4A:
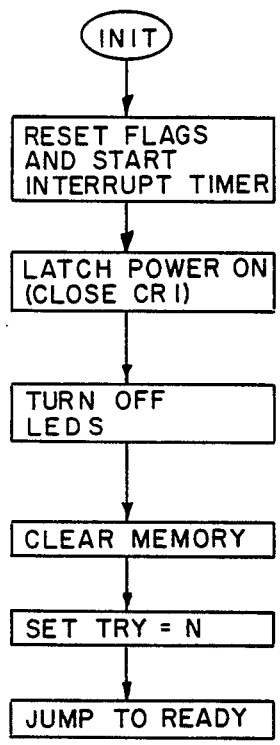
Figure 4B:
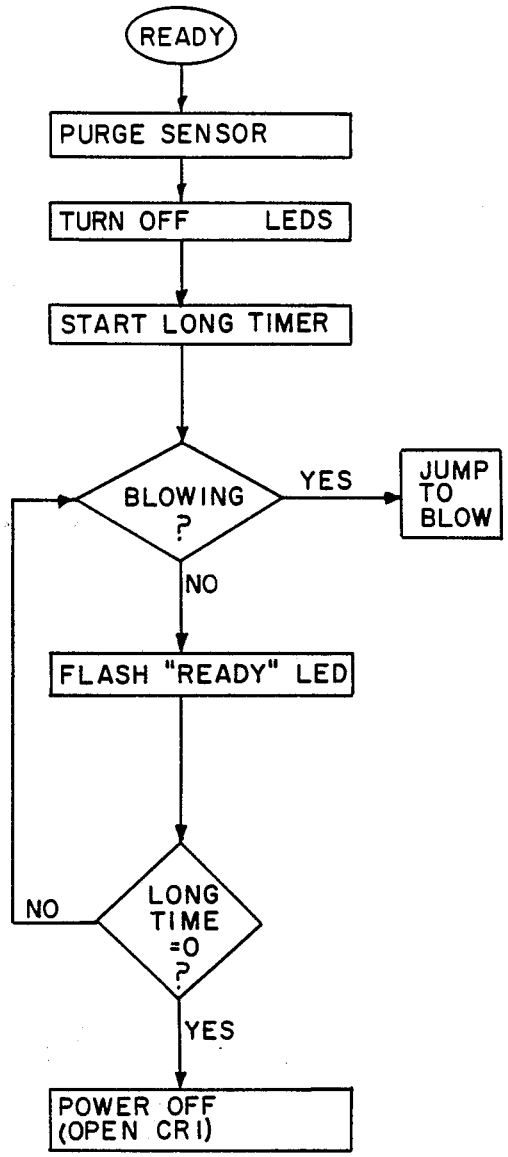

When C.P.U. 33 is first energized, it begins operation with an initialization routine INIT, the basic steps of which are depicted in FIG. 4A. C.P.U. 33 first resets all internal flags and starts operation of its internal interrupt timer in order to enable C.P.U. 33 to respond to interrupt requests. Next, C.P.U. 33 generates a signal at pin DB7 to energize relay CRI 103 in order to latch power to the system "ON". If required, "PASS", "WARN", and "FAIL" LED's 97, 98, and 99 respectively are switched off and the data memory of C.P.U. 33 is cleared. Next, the number of attempts allowed for successfully completing the identity-confirming act is set by loading a register designated TRY with a value N which is a positive integer whose value is less than the number of attempts most persons require to learn the identity-confirming act. For a confirming act of a given degree of difficulty, lowering the valve of N decreases the probability that the interlock 15 will be successfully defeated while increasing N increases the probability that interlock 15 will be successfuly defeated. Preferably, the degree of difficulty of the identity-confirming act empirically determined to be such that adequate security may be provided by setting N equal to 3. C.P.U. 33 then proceeds to the READY subroutine depicted in FIG. 4B.

To prepare alcohol sensor 67 for operation, C.P.U. 33 purges alcohol sensing element 73. The purge sequence begins by causing signal 39 received at the base of transistor Q4 70 to assume a high duty cycle, thereby causing the low voltage signal on line 69 to likewise assume a high duty cycle. Alcohol sensing element 73 is heated by heater 68 until its surface temperature is within the range of 200° C.–400° C. and is preferably in excess of 300° C. This causes any alcohol or other volatile substances to be desorbed from element 73. After the high duty cycle has been maintained for a time sufficient to purge element 73 which is preferably about 40 seconds, C.P.U. 33 reduces the duty cycle of signal 39 as to decrease the temperature of alcohol sensing element 73. The duty cycle of the output of regulator 35 remains at the reduced level until pressure switch 65 closes, thereby indicating commencement of a test, at which time C.P.U. 33 regulates the duty cycle of signal 39 as required to keep sensing element 73 at substantially the same temperature during delivery of a breath sample as existed prior thereto.

Figure 4C:
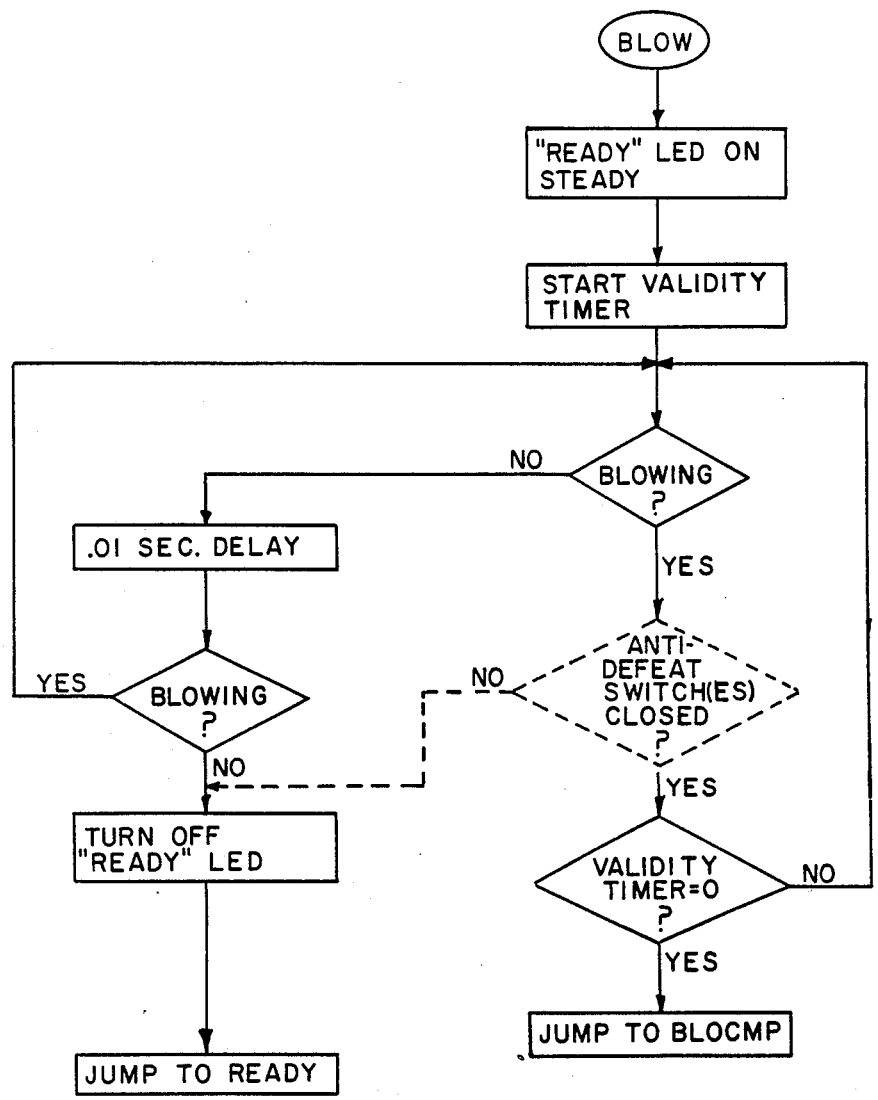
Figure 4D:
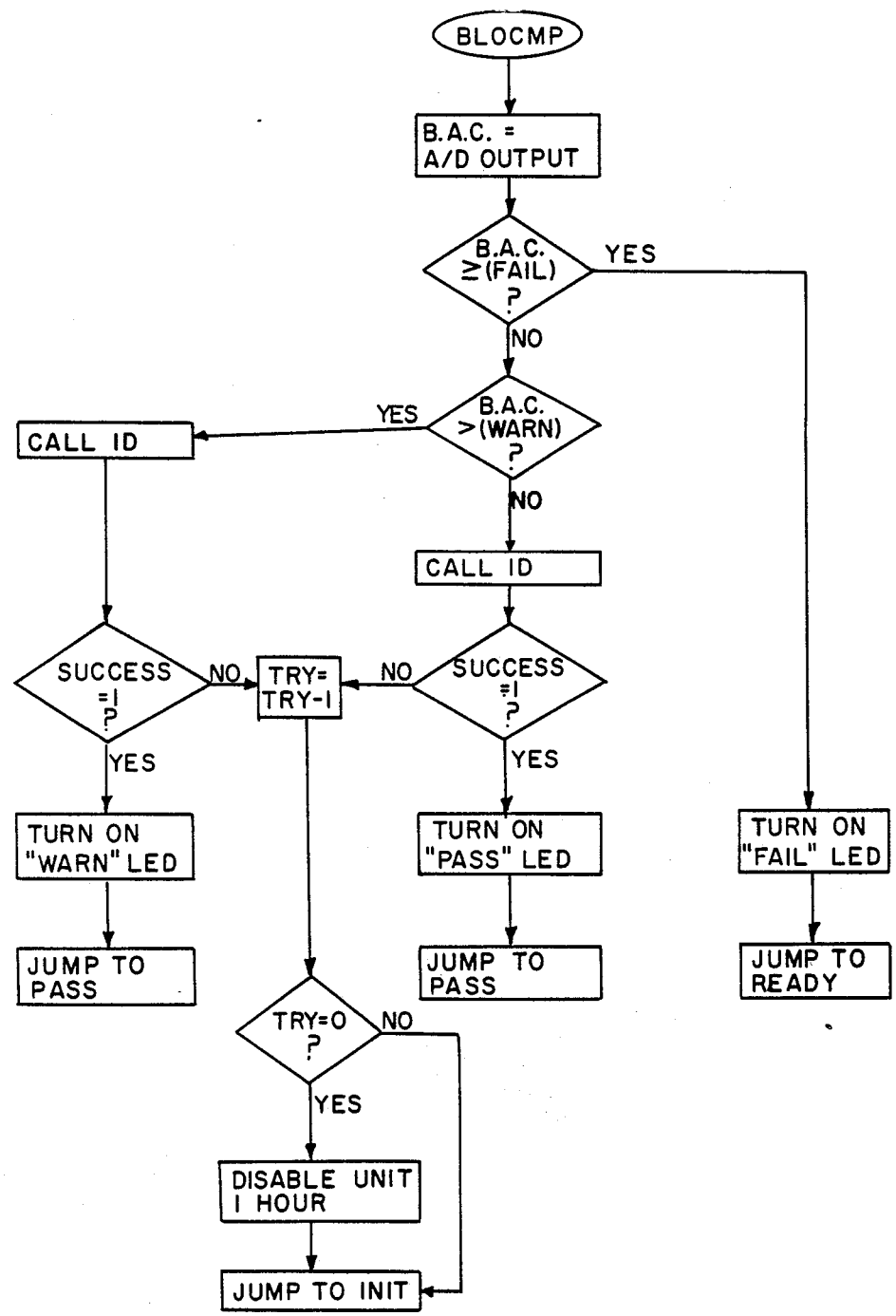

Once the purge sequence is completed, "PASS", "WARN", and "FAIL" LED's 97, 98, and 99 respectively are turned off if they have been on. As mentioned previously, "ON" LED 96 is on at all times while interlock 15 is energized. C.P.U. 33 then loads a value designated "LONG TIME" into an internal timer and starts the timer running, counting down from the loaded value to 0. If interlock 15 is not used within the period designated "LONG TIME", which is preferably on the order of 14 hours, interlock 15 is powered down by opening relay CR1 103 in order to conserve vehicle battery 30. During "LONG TIME", C.P.U. 33 causes "Ready" LED 24 to flash, indicating that interlock 15 is ready to receive a breath sample. If C.P.U. 33 senses blowing of a breath sample as indicated by the closing of pressure switch 65 before the "LONGTIME" period is over, the program jumps to a routine designated BLOW as depicted in FIG. 4C and described below.

Once pressure switch 65 closes, "Ready" LED 24 stops flashing and is lighted steadily. When this occurs, C.P.U. 33 sets a timer to insure that the flow of breath is continuous and uninterrupted for a period of time sufficient to insure a deep lung sample. This length of time is designated as the "validity time". If pressure switch 65 opens prior to the end of the validity time, thereby indicating that blowing has been interrupted, "Ready" LED 24 is turned off and the program then jumps back to the READY routine. If the flow of breath is sufficient to keep pressure switch 65 closed for the entire length of the validity time, the program then jumps to a "blow complete" routine designated BLOCMP shown in FIG. 4D to which reference is now made.

At the end of the validity time, C.P.U. 33 reads B.A.C. signal 44 from the data out (D O) port 92 of A/D converter 45 and compares its magnitude to at least one of two internally stored limits designated (FAIL) and (WARN). The (FAIL) limit is greater than the (WARN) limit and preferably corresponds to the maximum legal blood alcohol content. The (WARN) limit is preferably selected to correspond to a blood alcohol concentration at which most drivers are somewhat impaired but no legally considered incapable of driving. Typically, (FAIL) is selected to correspond to 0.1% blood alcohol concentration while (WARN) is selected to correspond to 0.05% blood alcohol concentration. If B.A.C. signal 44 is greater than or equal to (FAIL), C.P.U. 33 causes (FAIL) LED 99 to be turned on and jumps to the "Ready" routine described above. If B.A.C. signal 44 does not equal or exceed the (FAIL) limit, C.P.U. 33 determines whether the (WARN) limit is exceeded. If so, C.P.U. 33 calls the identity-confirmation subroutine ID to be described hereafter. If the identity of the operator is confirmed, C.P.U. 33 causes "WARN" LED 98 to turn on and jump to a routine designated PASS which will also be described further below. If the attempt at performing the identity-confirming act is unsuccessful, C.P.U. 33 decrements the TRY register and tests to see if the allowed number of tries at confirming the operator's identity has been exhausted. If the allowed number of tries has been exhausted, the unit is disabled for one hour or other period of sufficient duration to deter a person other than the designated operator from learning the identity-confirming act by being able to try the act repeatedly over a short period of time. If the allowed number of tries has not been exhausted, interlock 15 is re-initialized by way of the INIT routine. This requires the operator to deliver a new valid breath sample before another attempt at performing the identity-confirming act can be made. If B.A.C. signal 44 does not exceed the "WARN" level, the identity-confirmation subroutine ID is again called. If the identity-confirming act is performed successfully, "PASS" LED 97 is lighted and the program jumps to the PASS routine. Otherwise, the TRY register is again decremented and the unit is disabled for one hour if the allowed number of attempts have been exhausted.

Figure 4E:
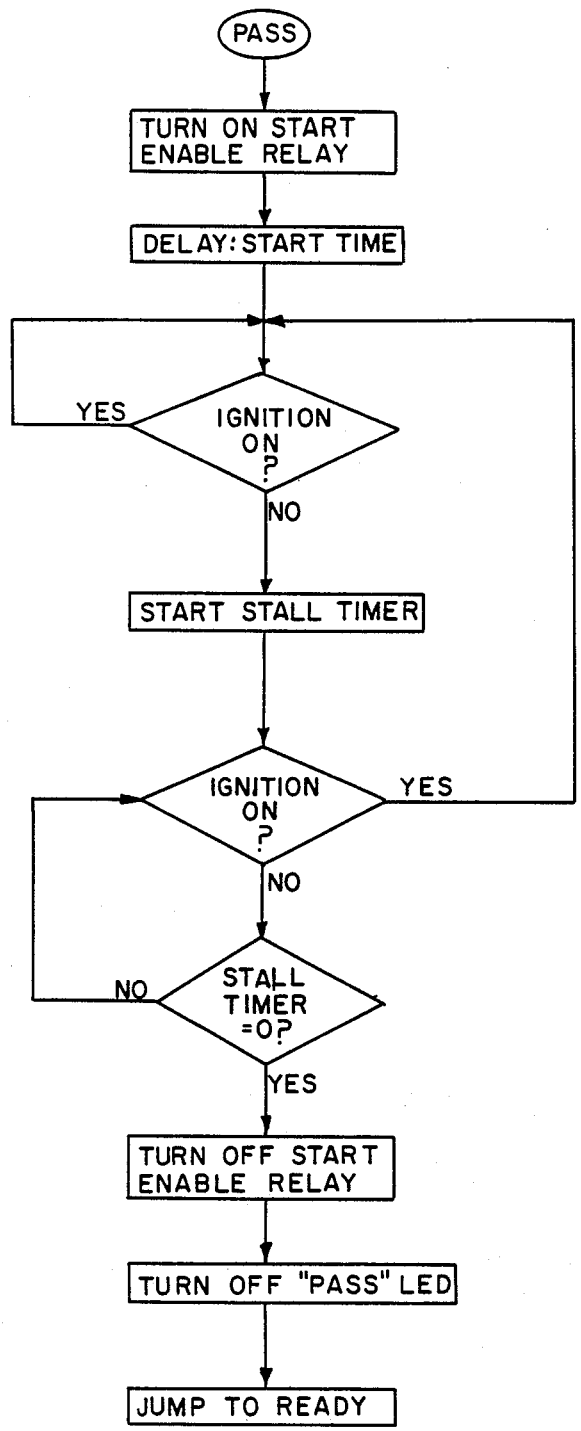

The PASS routine is now described with reference to FIG. 4E. When the PASS routine is entered, start enable relay 54 is energized thereby connecting ignition key switch 56 with starter solenoid 57 as to permit the vehicle to be started. Start enable relay 54 is enabled for a period designated "START TIME" which is preferably 30 to 60 seconds. This deters an operator who has successfully passed a sobriety test from leaving the vehicle to imbibe. If C.P.U. 33 senses, by way of wire 59, that ignition system 19 is not on after completion of the "START TIME" delay, the vehicle may have stalled. If the vehicle stalls on a freeway or in another potentially hazardous location, it might be unsafe to require a new test to permit the vehicle to be restarted. Accordingly, C.P.U. 33 starts a "STALL TIMER" which permits the vehicle to be restarted after stalling within a period which is preferably about 30 seconds. If vehicle ignition system 19 is still off at the end of that period, C.P.U. 33 deenergizes start enable relay 54 and turns off "PASS" LED 97 and jumps back to the READY routine thereby requiring a new test before the vehicle may again be started.

Figure 4F:
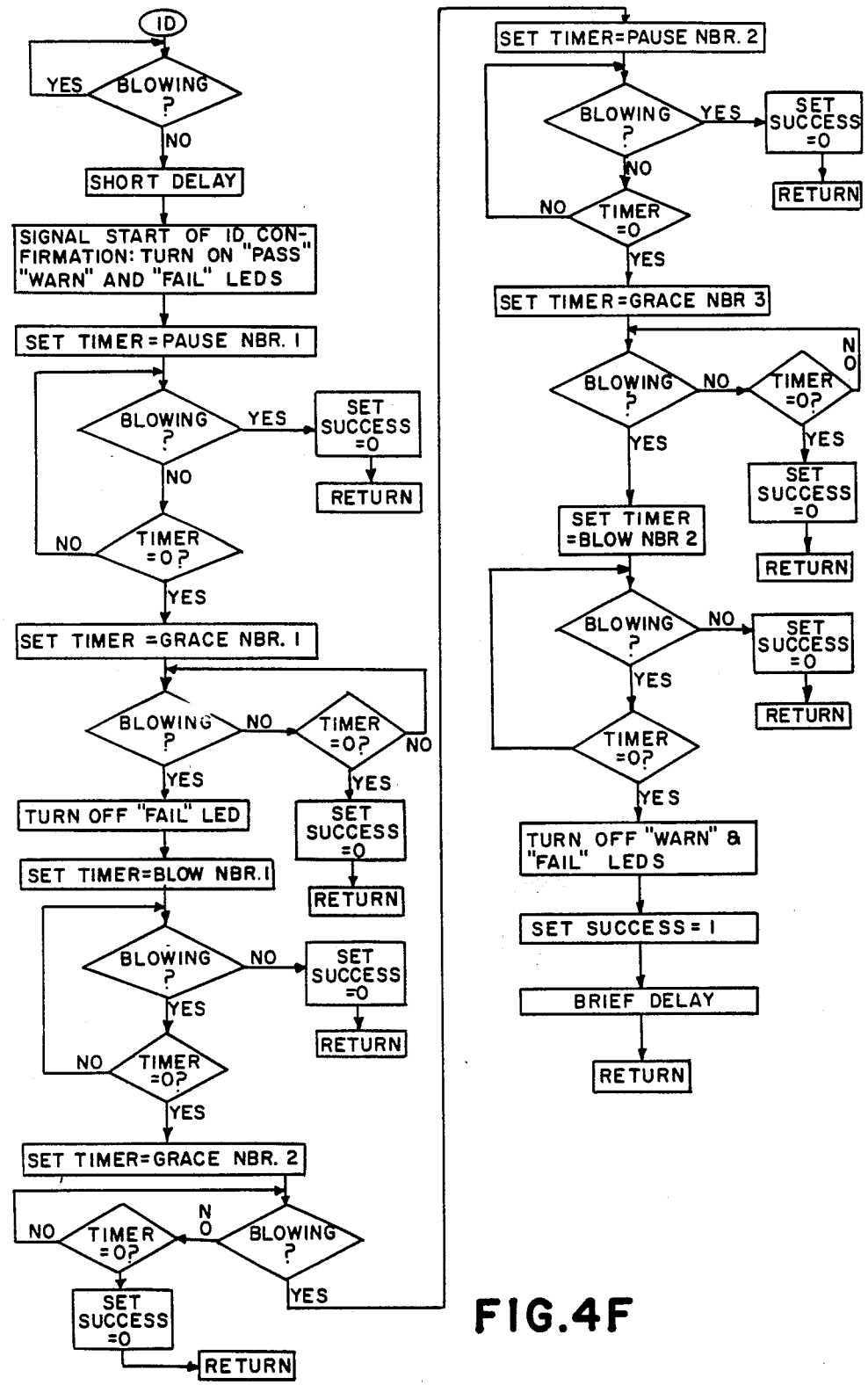

The identity-confirmation subroutine ID may be understood with reference to FIG. 4F which is a flow-chart representing the identity-confirmation act depicted in FIG. 3 wherein breath sample delivery has been completed during interval A. When blowing of a breath sample ceases, as indicated by an opening of pressure switch 65, C.P.U. 33 signals the operator to begin the identity-confirming act by turning on the "PASS", "WARN", and "FAIL" LED's 97, 98, and 99 respectively after a short delay. As noted above, this short delay should be a time insufficient to permit sampling head 16 to be passed from one person to another as to prevent another from delivering the breath sample and then passing the sampling head 16 to the designated operator to perform the identity-confirming act. After the start signal, the operator must refrain from blowing for a first pause period designated $P_1$. If pressure switch 65 closes during pause $P_1$, a flag designated SUCCESS is set equal to zero indicating that the identity of the operator has not been confirmed, in which event the program returns to the BLOCMP routine at the point from which subroutine ID was called and a new breath sample must be taken before the identity-confirming act can be tried again. If pressure switch 65 remains open for at least the duration of $P_1$, C.P.U. sets a timer equal to first grace period $G_1$. If the first blow, $B_1$, does not commence by the end of $G_1$, SUCCESS is set equal to zero and the program returns. Otherwise, C.P.U. 33 causes "FAIL" LED 99 to turn off to indicate to the operator that a portion of the identity-confirming act has been successfully completed. C.P.U. 33 then sets an internal timer to time the duration of $B_1$. If blowing does not continue for at least that period, the SUCCESS flag is set equal to zero and the program returns. If blowing is sustained for at least as long as required by the timer, the timer is then set to time grace period $G_2$. Blowing must cease prior to the end of $G_2$. If it does not, the SUCCESS flag is set equal to zero and the program returns. If blowing does cease by the end of $G_2$, C.P.U. 33 sets its timer to time the duration of a second pause, $P_2$. If blowing commences before the end of $P_2$, the SUCCESS flag is set equal to zero and the program returns. If pressure switch 65 does not sense blowing during $P_2$, the timer is set to a third grce period, $G_3$. If pressure switch 65 fails to sense blowing by the end of grace period $G_3$, the SUCCESS flag is set equal to zero and the program returns. Otherwise, the timer is set to time the second blow $B_2$. If the second blow is sustained at least until the timer times out, "WARN" and "FAIL" LED's 98 and 99 are briefly turned off indicating to the operator successfully completion of the identity-confirming act. The SUCCESS flag is then set equal to one and the program returns to the BLOCMP routine at the point from which subroutine ID was called. With the identify confirming act successfully completed, the BLOCMP routine is completed by turning on "Warn" LED 98 if B.A.C. signal 44 exceeds the (WARN) limit or turning on the "PASS" LED 97 if B.A.C. signal 44 does not exceed the (WARN) limit. In either of these two cases, the program then jumps to the PASS routine described above which causes start enable relay 54 to be energized, thereby permitting the vehicle to be started.

SECOND PREFERRED EMBODIMENT

Figure 5:
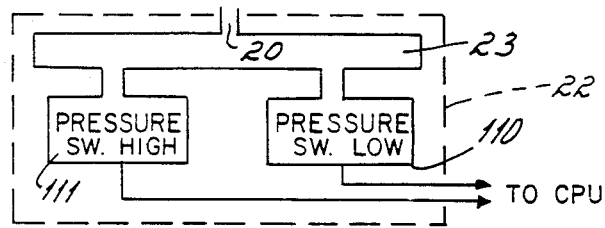
FIG. 5 is a block diagram of a portion of a sobriety interlock system illustrating a second preferred embodiment of a sobriety interlock system of the type shown in FIG. 1.
Figure 6:
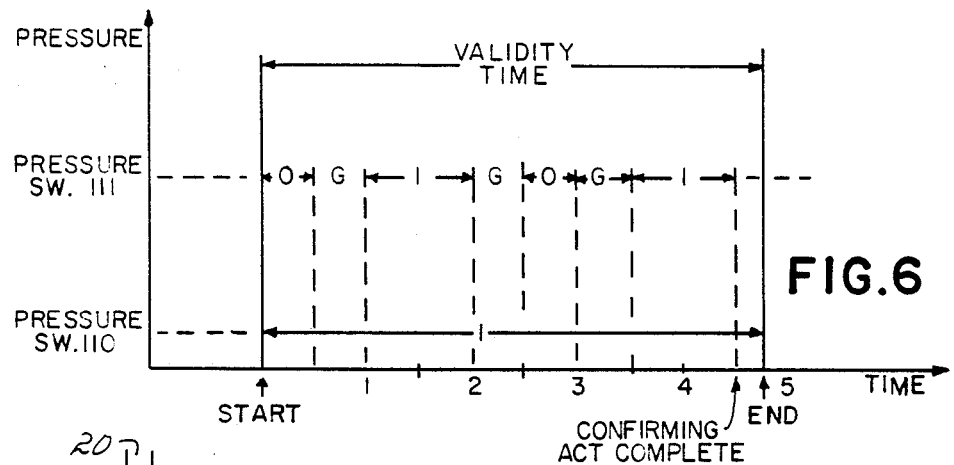
FIG. 6 is a timing diagram illustrating the operation of the embodiment illustrated in FIG. 5.

In light of the foregoing, a second preferred embodiment of the invention of FIG. 1 may be understood with additional reference to FIGS. 5 and 6. FIG. 5 shows an alternative breath sample validity/identity-confirmation sensing apparatus 22 for performing an identity-confirming act as illustrated by the timing diagram of FIG. 6. Unlike the first preferred embodiment which requires the confirming act to be performed at least partially before or after delivery of a breath sample if pressure switch 65 is to be used both for sample validity sensing and identity-confirmation sensing, the arrangement shown in FIG. 5 permits identity confirmation to take at any desired time before, after or during delivery of a breath sample. This fact should be noted even though the remaining description assumes that identity confirmation takes place during breath sample delivery.

As shown in FIG. 5, the interlock 15 of FIG. 1 may be equipped with an alternative form of sample validity/identity confirmation sensing means 22 comprising a "low" pressure switch 110 and a "high" pressure switch 111 having a higher switching pressure threshold than pressure switch 110. Pressure switches 110 and 111 both communicate with breath inlet port 20 by way of manifold 23 in order to sense the flow of breath into port 20. The switching threshold of "low" pressure switch 110 is selected in accordance with the resistance to the flow of breath through port 20 as to insure a deep lung sample of breath is delivered when low pressure switch 110 is held closed for validity time which is preferably 4.5 to 5.0 seconds in duration.

Referring now to FIG. 6 it can be appreciated that identity-confirmation sensing may take place substantially contemporaneously with sample validity sensing thereby advantageously minimizing the overall time required to perform a test. Anytime after the interlock 15 is prepared to receive a breath sample as indicated by the flashing of "Ready" LED 24, the operator may begin to blow into breath inlet port 20. For the entire period between the start and end of the validity time, the flow of breath must be sufficient to keep pressure switch "low" 110 in a closed (1) state as shown, thereby insuring a deep lung sample of breath.

The identity-confirming act is performed by modulating the flow of breath to close pressure switch "high" 111 according to a pattern which can be recognized by C.P.U. 33. In the example shown in FIG. 6, pressure switch 111 must be initially in an open (0) state for a period of at least 0.5 seconds. After a grace period of 0.5 seconds, pressure switch 111 must assume a closed state for at least a full second. Following another 0.5 second grace period, pressure switch must again open for 0.5 seconds then, after a third grace period, close for a full second. At the successful conclusion of this sequence the operator's identity is confirmed by C.P.U. 33. While the validity time period is shown in FIG. 6 as extending slightly beyond the completion of the identity-confirming act, any desired relative temporal relationship between the validity time period and the confirming act can be used.

THIRD PREFERRED EMBODIMENT

A third preferred embodiment of the invention wherein the confirming act may also be performed at any desired time before, during or after delivery of a breath sample can be understood in light of the above with particular reference to FIGS. 1, 7, 8, and 9.

Figure 7:
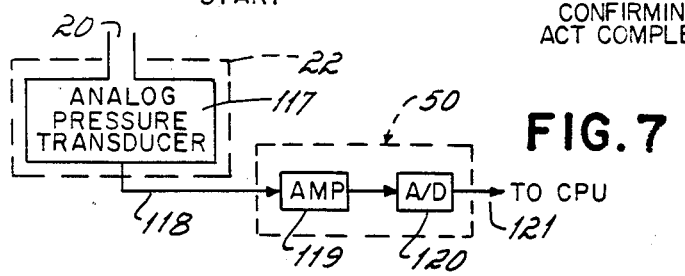
FIG. 7 is a block diagram of a portion of a sobriety interlock system illustrating a third preferred embodiment of a sobriety interlock system of the type illustrated in FIG. 1.

Referring now to FIGS. 1 and 7, the invention further contemplates the use of an analog pressure transducer 117 as sample validity/identity confirmation sensing means 22. Preferably analog pressure transducer 117 is an integrated circuit piezoresistive pressure sensor such as part number SX01 manufactured by SenSym connected in a pressure sensing relationship with breath inlet port 20. Transducer 117 generates an analog pressure signal 118 correlated to the flow of breath through port 20. Signal is received by signal processing means 50 which comprises an amplifier 119 connected to a second analog to digital (A/D) converter 120 which generates a digital pressure signal 121 which is received by C.P.U. 33.

Stored in the memory of C.P.U. 33 are HIGH and LOW threshold values against which digital pressure signal 121 can be compared for the purposes of performing identity confirmation and determining breath sample validity respectively. The HIGH and LOW threshold values are selected in a manner corresponding to the selection of the switching threshold pressures of pressure switches 111 and 110 of the second preferred embodiment described above. To facilitate comparison of the third and second preferred embodiments, the timing diagram of FIG. 8 uses the same exemplary identity confirming act as was described with reference to FIG. 6. Accordingly, there is no need to repeat the description of the identity-confirming act.

Figure 8:
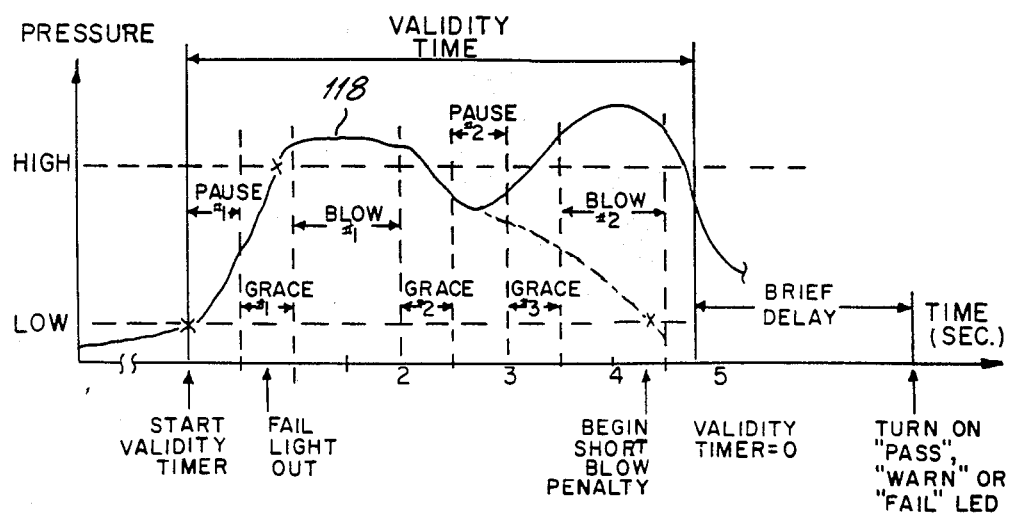
FIG. 8 is a timing diagram illustrating the operation of the embodiment of FIG. 7.

Referring now to FIG. 8, the operator may begin blowing a breath sample into port 22 at any time after "Ready" LED 24 begins flashing. When the validity timer of C.P.U. 33 starts, analog pressure signal 118 must equal or exceed the LOW threshold value. If, at any time while the validity timer is running, pressure signal 118 drops below the LOW threshold, as, for example, is indicated by the dashed line, the test will be aborted. Assuming all available attempts have not been exhausted, (i.e. TRY≠0) the test may be repeated. Assuming that the operator performs the identity confirming act successfully while maintaining a sufficient flow of breath so that pressure signal 121 exceeds the LOW threshold during the entire validity time, the result of the sobriety test will be displayed by LEDs 52 and start enable relay 54 energized if the sobriety test is passed. The "Fail" LED 99 will be extinguished when the first blow commences after successful completion of the first pause. After successful completion of the second pause and second blow, C.P.U. 33 then confirms the identity of the operator. After the validity timer times out, the result of the alcohol breath test will be indicated by lighting either the "PASS" 97, "WARN" 98 or "FAIL" 99 LED as appropriate following a brief delay. If the alcohol level is below the level required to light "FAIL" LED 99, start enable relay 54 is energized to permit the vehicle to be started.

FOURTH PREFERRED EMBODIMENT

Figure 9:
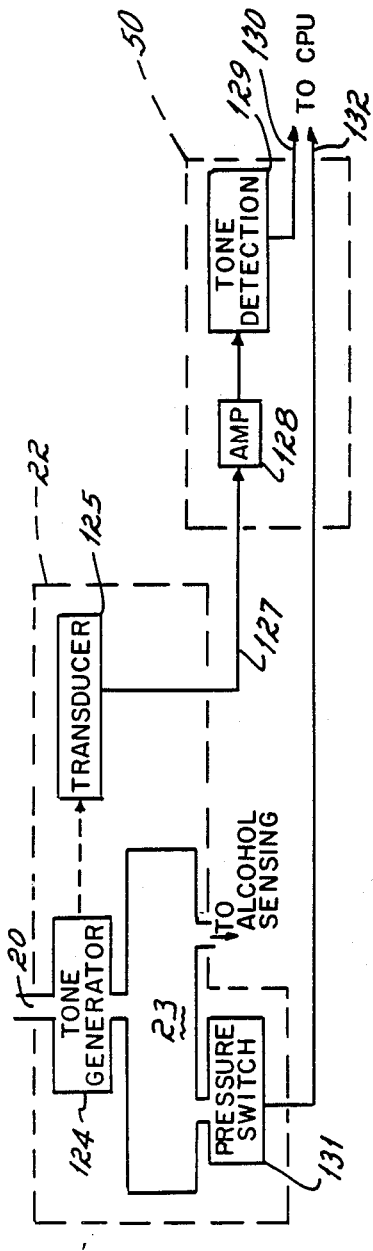
FIG. 9 is a block diagram of a portion of a sobriety interlock system illustrating a fourth preferred embodiment of a sobriety interlock of the type illustrated in FIG. 1.

In light of the foregoing, a fourth preferred embodiment of the invention may be understood with particular reference now to FIGS. 1 and 9. The invention further contemplates alternative sample validity/identity confirmation sensing means 22 wherein a tone generator 124 operably connected with breath inlet port 20 can be used to perform one or both sensing functions. Tone generator 124 is a device which can be blown into to generate at least one tone lying within a predetermined frequency range such that the designated operator can be trained to perform a suitable identity confirming act involving the generation of one or more such tones in a manner detectable by C.P.U. 33. Preferably, tone generator 124 is such that generation of the proper tone requires a level of skill which is not readily acquired by most persons within the number of tries at performing the identity-confirming act allowed by C.P.U. 33. Tone generator 124 may comprise for example, a vibratable reed device similar to a clarinet or oboe mouthpiece, an orifice and tube arrangement along the lines of a flute or a mouthpiece similar to the type used on a brass instrument such as a trumpet or trombone. Regardless of the particular configuration of tone generator 124, the skill inherently required of the identity-confirming act may reside either in the difficulty in generating one or more particular tones, either alone or in sequence or, in the timing pattern and/or amplitude of such tones. in light of the present disclosure, it will be apparent to one skilled in the art that a wide variety of other types of tone generating apparatus may be employed to implement this embodiment of the invention.

As indicated by the dashed arrow in FIG. 9, tone generator 124 is operably connected in a tone sensing relationship with a transducer 125 such as a microphone which converts tones produced by tone generator 124 into a tone signal 127 which is received by signal processing means 50 which comprises an amplifier and tone detection means 129 operable to generate at least one "tone detected" signal 130 when tone generator 124 produces tones lying within one or more predetermined frequency ranges.

Sample validity/identity confirmation means 22 may also include a pressure switch 131 operable to generate a pressure signal 132 for sample validity sensing to be performed as previously described. Where pressure switch 131 is sued to handle breath sample validity sensing, tone generator 124 can be used to perform identity confirmation at any desired time before during or after delivery of a breath sample by requiring the designated operator to generate one or more tones in a particular manner detectable by C.P.U. 33. For example, tone generator 124 may be used to generate a single tone lying within a predetermined range of frequencies and C.P.U. 33 can be programmed to detect an identity-confirming act wherein the tone must be present and/or absent for one or more intervals of specified duration. Alternatively, C.P.U 33 can be programmed to detect a series of different tones played in a particualr sequence. It may also be desirable to require the tones in such a sequence to be played with particular timing requirements in a manner similar to the beats of the notes in a musical tune. Where the identity-confirming act requires tones to be delivered at times overlapping delivery of a breath sample, the act must be such that sufficient breath flow is maintained to keep pressure switch 131 closed during delivery of the breath sample as to insure its validity.

In yet another preferred embodiment, pressure switch 131 may be omitted and tone generator 124 used to perform both sample validity and identity confirmation sensing. This may be accomplished by requiring at least one tone to be present continuously during delivery of a breath sample for at least the entire validity time. Identity confirmation can be accomplished at any desired time. If identity confirmation is to be performed during the delivery of a breath sample, this can be accomplished by requiring the tone to vary in pitch in a predetermined manner recognizable by C.P.U. 33 or by requiring the generation of a tone lying within a particular frequency range from among many possible tones. This assumes that tone generator 124 is such that the mere presence of the proper tone necessarily indicates a flow of breath sufficient, if sustained for the entire validity time, to insure a deep lung sample of breath. If this assumption is not valid but tone generator 124 is such that the amplitude of the tone produced is correlated to the amount of breath flow into port 20, breath sample validity can be assured another way. C.P.U. 33 can be connected to transducer 125 and programmed so that tone signal 127 must be sustained above a minimum amplitude for the entire validity time. The minimum amplitude of tone signal 127 is selected to correspond to an amount of breath flow which, if sustained for the entire validity time, insures a valid breath sample.

FIFTH PREFERRED EMBODIMENT

Figure 10:
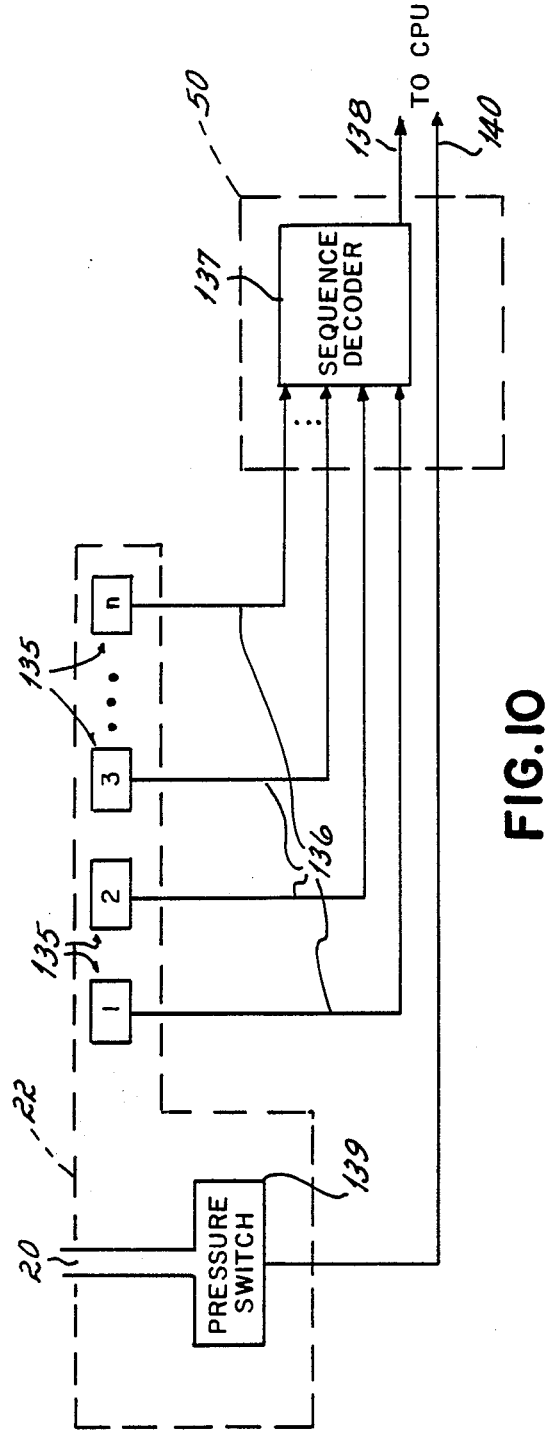
FIG. 10 is a block diagram of a portion of a sobriety interlock system illustrating a fifth preferred embodiment of a sobriety interlock of the type illustrated in FIG. 1.

In light of the foregoing, a fifth preferred embodiment of the invention may be understood with particular reference now to FIGS. 1 and 10. According to the invention, yet another form of sample validity/identity confirmation sensing means comprises a pressure switch 139 operably connected with breath inlet port 20 and a plurality of finger actuated switches 135, each of which generates a corresponding switch signal 136 received by a sequence decoder 137 which generates a sequence detected signal 138 when switches 135 have been actuated in the particular manner according to which the identity-confirming act is defined. The identity-confirming act recognizable by decoder 137 may be defined in terms of a required sequence and/or duration of actuation of one or more of switches 135 beginning at any desired time before during or after delivery of a breath sample.

Alternatively, sequence decoder 137 may be omitted and its function performed by C.P.U. 33 which can be wired to receive signals 136 directly. In either case, signal 140 serves to communicate the state of pressure switch 139 to C.P.U. 33 which determines whether a breath a sample is valid in the manner previously described.

SIXTH PREFERRED EMBODIMENT

In light of the foregoing, a sixth preferred embodiment of the invention may be understood with particular reference now to FIGS. 1 and 4. In order to prevent any of the above-described embodiments of interlock system 15 from being defeated by blowing a gas other than breath into the breath inlet port 20 of sampling head 16, an anti-defeat switch 150 may be connected between 5 Volt regulator 34 and an input port of C.P.U. 33 as shown in dashed lines in FIG. 1. Anti-defeat switch 150 is a normally-open, momentary-contact switch which is physically located some distance away from, but within arms reach of, sampling head 16. Preferably, anti-defeat switch 150 is located on main control module 17 in a position accessible to a person seated in the driver's seat when control module 17 is installed in its normal location under the dash of the interlocked vehicle.

In operation, the input port of C.P.U. 33 connected to anti-defeat switch 150 will be at a logical "one" state when anti-defeat switch 150 is held closed and will be at a logical "zero" state at all other times. If anti-defeat switch 150 is used, the program of C.P.U. 33 is altered as indicated by the dashed lines in the flowchart of FIG. 4C. Once delivery of a gas sample to breath inlet port 20 commences (Blowing?=YES), C.P.U. 33 interrogates the status of anti-defeat switch 150. If anti-defeat switch is not closed (Anti Defeat Switch Closed?=No) continuously for the entire validity time, C.P.U. 33 turns "Ready" LED 24 off and jumps to the READY routine, thereby aborting the test. On the other hand, if anti-defeat switch 150 is held closed continuously for the entire validity time, the remainder of the test proceeds normally.

Since anti-defeat switch 150 is located away from sampling head 16, it would be very difficult for a person to hold anti-defeat switch 150 closed while manipulating means such as a balloon or bicycle pump in the manner required to deliver a deceptive gas sample to breath inlet port 20 located on sampling head 16. In this way, anti-defeat switch 150 helps to insure that the gas delivered to breath inlet port 20 is a contemporaneous breath sample rather than some other gas, such as air from a previously-inflated balloon or bicycle pump. In order to even more effectively deter defeat of interlock 15 by delivering a deceptive gas sample expelled from a bicycle pump or previously-inflated balloon, anti-defeat switch 150 can be supplemented with a second anti-defeat switch 155 connected between another input port of C.P.U. 33 and the 5 V supply by way of line 156 of cable 18 as illustrated by dashed lines in FIG. 1. Alternatively, second anti-defeat switch 155 could be wired in series with anti-defeat switch 150. In either case, second anti-defeat switch 155 is physically located on sampling head 16 as to be actuable with one hand while holding sampling head 16 with the same hand. Second anti-defeat switch 155 is also a normally-open, momentary-contact switch.

In operation, C.P.U. 33 is to interrogate the status of both anti-defeat switches 150 and 155 during the delivery of a gas sample into breath inlet port 20. If both anti-defeat switches do not remain closed continuously for the entire validity time, C.P.U. 33 turns "Ready" LED 24 off and jumps to the READY routine, thereby aborting the test. Testing proceeds normally only if both anti-defeat switches 150 and 155 are held closed continuously for the entire validity time.

Since second anti-defeat switch 155 is located on sampling head 16 and anti-defeat switch 150 is located some distance away, preferably on control module 17, requiring both switches 150, 155 to be actuated provides some assurance that both hands of the operator are occupied and are therefore unavailable to manipulate deceptive gas delivery means such as a balloon or bicycle pump.

While the above descriptions constitute several preferred embodiments of the apparatus and method of the invention, it is to be understood that the invention is not limited thereby and that in light of the present disclosure of the invention various other alternative embodiments will be apparent to persons skilled in the art. Accordingly, it is to be understood that changes may be made without departing from the scope of the invention as particularly pointed out and distinctly claimed in the claims set forth below.

What is claimed is:

1. A method of avoiding circumvention of a vehicle sobriety interlock by confirming that the operator thereof is a designated operator, said method comprising the steps of:
    (a) monitoring the performance of an identity confirming physical act by the operator, said identity confirming act requiring a sufficient degree of skill as to be incapable of performance in fewer than a predetermined number of attempts by substantially all persons other than designated operators who possess said degree of skill;
    (b) determining whether said identity confirming physical act is correctly performed by the operator in fewer than said predetermined number of attempts and, if so,
    (c) generating an identity-confirmation signal as a precondition for enabling a vehicle connected to the interlock to be started if the operator also delivers a breath sample to the interlock having an alcohol level sufficiently low to pass a breath sobriety test.

2. The method of claim 1 further comprising the step of preventing a vehicle from starting unless said breath sobriety test is based on a deep lung sample of breath.

3. The method of claim 2 wherein said step of preventing the vehicle from starting unless said breath sobriety test is based on a deep lung sample of breath comprises the steps of:
    (a) determining whether said sample is delivered with an essentially continuous uninterrupted flow of breath of specified duration, and if not,
    (b) preventing generation of a signal responsive to permit starting of the vehicle.

4. The method of claim 3 wherein said specified duration is at least four seconds.

5. The method of claim 1 wherein said physical act requires exhaling into said apparatus at the same location where breath samples are delivered and is performed at least partially during delivery of a breath sample for sobriety testing in order to prevent said physical act from being performed by a person other than the one delivering said breath sample.

6. The method of claim 1 wherein said physical act requires exhaling into said sobriety interlock at the same location where breath samples are delivered and is completed before delivery of a breath sample for sobriety testing commences, the time period between completion of said physical act and commencement of delivery of said breath sample being sufficiently short as to prevent said physical act from being performed by a person other than the one delivering the breath sample.

7. The method of claim 1 wherein said physical act requires exhaling into said sobriety interlock at the same location where breath samples are delivered and is commenced after delivery of a breath sample for sobriety testing is completed, the time period between completion of delivery of said breath sample and commencement of said physical act being sufficiently short as to prevent said physical act from being performed by a person other than the one delivering the breath sample.

8. The method of claim 1 wherein said physical act comprises:
    blowing at least one burst of breath of specific duration into said sobriety interlock.

9. The method of claim 1 wherein said physical act comprises:
    blowing a plurality of bursts of breath with pauses therebetween into said sobriety interlock, at least one of said bursts of breath being of specified duration.

10. The method of claim 9 wherein at least one of said bursts of breath is preceded by a grace period, said identity-confirmation signal being generated only if said burst commences at least by the conclusion of said grace period.

11. The method of claim 1 wherein said physical act comprises:
blowing a plurality of bursts of breath with pauses therebetween into said sobriety interlock, at least one of said pauses being of specified duration.

12. The method of claim 11 wherein at least one of said pauses is preceded by a grace period, said identity-confirmation signal being generated only if said pause commences at least by the conclusion of said grace period.

13. The method of claim 1 wherein said physical act comprises:
blowing a plurality of bursts of breath with spaces therebetween into said sobriety interlock, at least one of said bursts and at least one of said pauses being of specified duration.

14. The method of claim 1 wherein said physical act comprises:
using at least one of the lips, mouth, tongue and vocal chords to generate at least one tone within in a specified frequency range.

15. The method of claim 1 wherein said physical act comprises:
using at least one of, the lips, mouth, tongue, vocal chords and lungs, to generate at least one tone within a specified frequency range and at least partially concurrently therewith, actuating at least one switch.

16. The method of claim 15 further comprising the steps of:
(a) measuring the amplitude of a signal correlated to the amplitude of said tone, and
(b) generated a validity signal to satisfy a required condition for enabling the vehicle to be started when the amplitude of said signal is maintained above a predetermined magnitude for a period of time sufficient to insure a deep lung sample of breath.

17. The method of claim 1 wherein said physical act comprises:
coordinated blowing of breath into said interlock and actuating at least one switch by means other than blowing.

18. The method of claim 1 further comprising the step of providing at least one humanly perceptible indication when at least a portion of said physical act is performed correctly.

19. The method of claim 18 wherein said indication is not provided unless said breath sobriety test is passed before said physical act is attempted.

20. A method of confirming the identity of an operator of a sobriety interlock for a vehicle and assuring a deep lung sample of breath, comprising the steps of:
(a) monitoring the performance of an identity confirming physical act by the operator, said identity confirming act requiring a sufficient degree of skill as to be incapable of performance in fewer than a predetermined number of attempts by substantially all persons other than designated operators who possess said degree of skill;
(b) sensing a parameter correlated to the flow of breath to determine whether breath has been exhaled essentially continuously without interruption in excess of a minimum flow for at least a minimum period, said minimum flow and said minimum period having been selected to insure a deep lung sample of breath and, if so,
(c) generating a validity signal to satisfy a first required condition for enabling the vehicle to be started;
(d) determining whether said identity confirming physical act is performed in fewer than said predetermined number of attempts and if so,
(e) generating an identity-confirmation signal to satisfy a second required condition for enabling the vehicle to be started.

21. The method of claim 20 wherein said vehicle is enabled to be started only if both said first and second required conditions are satisfied by the same exhalation of breath.

22. The method of claim 20 further comprising the step of providing at least one humanly perceptible indication when at least a portion of said physical act is performed correctly.

23. The method of claim 22 wherein said indication is not provided unless said breath sobriety test is passed before said physical act is attempted.

24. An apparatus for avoiding circumvention of a vehicle sobriety interlock by confirming that the operator thereof is a designated operator, said apparatus comprising:
(a) identity-confirmation sensing means operable to monitor the performance of an identity confirming physical act by the operator, said identity confirming act requiring a sufficient degree of skill as to be incapable of performance in fewer than a predetermined number of attempts by substantially all persons other than designated operators who possess said degree of skill, and
(b) identity-confirmation signal generating means responsive to said confirmation sensing means for generating an identity-confirmation signal when said physical act has been performed in fewer than said predetermined number of attempts, generation of said identity-confirmation signal being a required condition for enabling the vehicle to be started.

25. The apparatus of claim 24 further comprising:
sample validity determining means for enabling the vehicle to be started only if said breath sobriety test is based on a deep lung sample of breath.

26. The apparatus of claim 25 wherein said sample validity determining means comprises:
(a) sample validity sensing means for sensing a parameter correlated to the flow of breath and
(b) validity signal generating means responsive to said sample validity sensing means to generate a validity signal when breath has been exhaled into the interlock essentially continuously without interruption at at least a minimum flow for at least a minimum time period, generation of said validity signal being a required condition for enabling the vehicle to be started.

27. The apparatus of claim 26 wherein said sample validity sensing means comprises a first pressure switch and said identity-confirmation sensing means comprises a second pressure switch, both of said pressure switches being operatively disposed to sense the flow of breath into said interlock, said second pressure switch having a higher switching pressure threshold than said second pressure switch.

28. The apparatus of claim 26 wherein said sample validity sensing means and said identity confirmation sensing means comprise at least one analog pressure sensor.

29. The apparatus of claim 28 wherein said analog pressure sensor comprises a piezoresistive pressure sensor.

30. The apparatus of claim 26 wherein said sample validity determining means comprises means to generate a tone in response to the flow of breath into the interlock.

31. The apparatus of claim 26 further comprising:
(a) anti-defeat means operably connected to said validity signal generating means so that said validity signal cannot be generated unless said anti-defeat means is continuously actuated during said time period.

32. The apparatus of claim 24 wherein said anti-defeat means comprises a momentary contact switch.

33. The apparatus of claim 24 wherein said anti-defeat means comprises a pair of momentary contact switches.

34. The apparatus of claim 24 wherein said identity-confirmation signal generating means is adapted to generate an identity-confirmation signal only when said physical act is performed at least partially temporally overlapping delivery of a breath sample for sobriety testing in order prevent said physcial act from being performed by a person other than the one delivering said breath sample.

35. The apparatus of claim 24 wherein said physical act requires exhaling into said apparatus at the same location where breath samples are delivered and wherein said indentity-confirmation signal generating means is adapted to generate an identity-confirmation signal when said physical act is completed before delivery of a breath sample for sobriety testing commences, the time period between completion of said physical act and commencement of delivery of said breath sample being sufficiently short as to prevent said physical act from being performed by a person other than the one delivering the breath sample.

36. The apparatus of claim 24 wherein said identity-confirmation sensing mans comprises:
flow sensing means operative to generate a blowing signal when the flow of breath into said apparatus is greater than or equal to a predetermined level.

37. The apparatus of claim 36 wherein said sample validity sensing means comprises at least one member of the group consisting of, a flow sensor, a pressure switch, an analog pressure sensor, a temperature sensor and a humidity sensor.

38. The apparatus of claim 36 wherein said identity-confirmation signal generating means comprises computing means responsive to said blowing signal to generate an identity-confirmation signal when said blowing signal comprises at least one pulse of specified duration.

39. The apparatus fo claim 36 wherein said identity-confirmation signal generating means comprises computing means responsive to said blowing signal to generate an identity-confirmation signal when said blowing signal comprises a plurality of pulses with pauses therebetween, at least one of said pauses being of specified duration.

40. The apparatus of claim 24 wherein said identity-confirmation sensing means comprises flow sensing means responsive to the flow of breath into the interlock and at least one switch actuated by means other than blowing breath into the interlock.

41. The apparatus of claim 40 wherein said flow sensing means comprises at least one member of the group consisting of, a flow sensor, a pressure switch, an analog pressure sensor and a humidity sensor.

42. The apparatus of claim 24 wherein said identity-confirmation sensing means comprises flow sensing means responsive to the flow of breath into the interlock and at least one switch actuated by means other than blowing breath into the interlock.

43. The apparatus of claim 24 wherein said identity-confirmation sensing means comprises means responsive to generate a tone using at least one of, the lips, mouth, tongue, vocal chords and lungs.

44. The apparatus of claim 24 further comprising means for providing at least one humanly perceptible indication when at least a portion of said physical act is performed correctly.

45. The apparatus of claim 44 wherein said indication is not provided unless said breath sobriety test is passed before said physical act is attempted.

46. A vehicle sobriety interlock method, comprising the steps of:
(a) measuring the alcohol content of a breath sample from an operator, then;
(b) determining whether said operator is a designated operator based on the ability of the operator to perform a predetermined identity confirming physical act in fewer than a predetermined number of attempts, said identity confirming act requiring a sufficient degree of skill as to be incapable of performance in fewer than said predetermined number of attempts by persons other than designated operators who possess such skill, said determining step being performed only if said alcohol content does not exceed a predetermined limit, then;
(c) permitting the vehicle to be started only if said operator is determined to be a designated operator after said alcohol content of said breath sample has been measured and found not to exceed said predetermined limit.

47. A sobriety interlock for a vehicle, comprising:
(a) measuring means for measuring the alcohol content of a breath sample from an operator;
(b) identity confirmation means for determining, whether said operator is a designated operator based on the ability of the operator to perform a predetermined identity confirming physical act in fewer than a predetermined number of attempts, a said identity confirming act requiring a sufficient degree of skill as to be incapable of performance in fewer than said predetermined number of attempts by persons other than designated operators who possess such skill;
(c) enabling means operably connected to said measuring means and said identity confirmation means to enable said identify confirmation means only if said alcohol content as measured by said measuring means does not exceed a predetermined limit; and
(d) means for permitting the vehicle to be started only if said operator is determined by said identity confirmation means to be a designated operator after said breath sample measured by said measuring means not to exceed said predetermined limit.

48. A vehicle sobriety interlock method, comprising the steps of:
(a) measuring the alcohol content of a breath sample from an operator, then;
(b) disabling identity confirmation means to prevent determining whether said operator is a designated operator only if said measured alcohol content exceeds a predetermined limit, otherwise;

(c) enabling identity confirmation means of said alcohol contant does not exceed said predetermined limit to determine whether said operator is a designated operator, then;

(d) permitting the vehicle to be started only if said operator is determined by said identity confirmation means to be a designated operator after said alcohol content of said breath sample measured by said measuring means has been found not to exceed said predetermined limit.

49. A sobriety interlock for a vehicle, comprising:
(a) measuring means for measuring the alcohol content of a breath sample from an operator;
(b) identity confirmation means for determining whether said operator is a designated operator based on the ability of the operator to perform a predetermined identity confirming physical act in fewer than a predetermined number of attempts, said identity confirming act requiring a sufficient degree of skill as to be incapable of performance in fewer than said predetermined number of attempts by persons other than designated operators who possess such skill;
(c) enabling means operably connected to said measuring means and said identity confirmation means to enable said identity confirmation means only if said alcohol content measured by said measuring means does not exceed a predetermined limit and otherwise, to disable said identity confirmation means; and
(d) means for permitting the vehicle to be started only if said operator is determined by said identity confirmation means to be a designated operator after said alcohol content of said breath sample measured by said measuring means has been found not to exceed said predetermined limit.

50. A method of avoiding circumvention of a vehicle sobriety interlock by confirming that the operator thereof is a designated skilled operator, said method comprising the steps of:
(a) monitoring the performance of an identity confirming physical act by the operator, wherein said identity confirming act can be learned by a previously unskilled operator only by attempting said act more than a predetermined number of times;
(b) determining whether said identity confirming physical act is correctly performed by the operator in fewer than said predetermined number of attempts and, if so,
(c) generating an identity-confirming signal as a precondition for enabling a vehicle connected to the interlock to be started if the operator also delivers a breath sample to the interlock having an alcohol level sufficiently low to pass a breath sobriety test.

51. A method of confirming the identity of an operator of a sobriety interlock for a vehicle and assuring a deep lung sample of breath, comprising the steps of:
(a) monitoring the performance of an identity confirming physical act by the operator, wherein said identity confirming act can be learned by a previously unskilled operator only by attempting said act more than a predetermined number of times;
(b) sensing a parameter correlated to the flow of breath to determine whether breath has been exhaled essentially continuously without interruption in excess of a minimum flow for a least of minimum period, said minimum flow and said minimum period having been selected to insure a deep lung sample of breath and, if so,
(c) generating a validity signal to satisfy a first required condition for enabling the vehicle to be started;
(d) determining whether said identity confirming physical act is performed in fewer than said predetermined number of times and if so,
(e) generating an identity-confirmation signal to satisfy a second required condition for enabling the vehicle to be started.

52. An apparatus for avoiding circumvention of a vehicle sobriety interlock by confirming that the operator thereof is a designated skilled operator, said apparatus comprising:
(a) identity-confirmation sensing means operable to monitor the performance of an identity confirming physical act by the skilled operator, wherein said identity confirming act can be learned by a previously unskilled operator only by attempting said act more than a predetermined number of times;
(b) identity-confirmation signal generating means responsive to said confirmation sensing means for generating an identity-confirmation signal when said physical act has been performed in fewer than said predetermined number of attempts, generation of said identity-confirmation signal being a required condition for enabling the vehicle to be started.

53. A sobriety interlock for a vehicle which requires operation by a skilled operator to enable vehicle operation said interlock comprising:
(a) means for confirming receipt of an acceptable breath sample;
(b) means for confirming the performance of an identity cofirming act by said skilled operator in fewer than a predetermined number of attempts, said act being incapable of performance by substantially all unskilled operators in less than said predetermined number of attempts, both confirmations being required for operation of said interlock to enable vehicle operation.

54. An interlock as in claim 53 wherein said identity confirming act can be learned by a previously unskilled person only by attempting said act more than said predetermined number of times.

55. A sobriety interlock for a vehicle, said sobriety interlock comprising:
(a) identity confirming means for monitoring the performance of an identity confirming physical act by a prospective operator and generating an identity confirmed signal upon performance of said act to satisfy a first necessary precondition for enabling said vehicle to be started, said identity confirming act requiring a sufficient degree of skill as to be incapable of performance by substantially all persons other than designated operators who possess said degree of skill;
(b) breath alcohol testing means adapted to receive a breath sample from the prospective operator and determining the alcohol content of said sample and, in the event said alcohol content is acceptable, generating a pass signal to satisfy a second necessary precondition for enabling said vehicle to be started; and
(c) enabling means connected to said identity confirming means and said breath alcohol testing means and connecting to the vehicle to enable the vehicle to be started when at least said first and second necessary preconditions have been satisfied.

56. The interlock of claim 55 further comprising means to insure said breath sample is a deep lung breath sample and, if so generate a validity signal as a third necessary precondition for enabling said vehicle to be started.

57. The interlock of claim 55 wherein said identity confirming means and said breath alcohol testing means include a common breath delivery port whereat said prospective operator must blow breath to deliver said breath sample and to perform said identity confirming act.

58. The interlock of claim 55 wherein said enabling means includes means for requiring at least a portion of identity confirming act to be performed substantially contemporaneously with at least a portion of delivery of said breath sample.

59. The interlock of claim 55 further including means for preventing starting of the vehicle for at least a predetermined period of time upon failure to perform said identity confirming act in fewer than a predetermined number of attempts regardless of whetehr any other preconditions for allowing the vehicle to start have been satisfied.

60. A sobriety interlock method for controlling starting of a vehicle, said method comprising the steps of:
 (a) confirming the identity of a prospective operator as a designated individual by requiring said operator to perform an identity confirming physical act, said act requiring a sufficient degree of skill as to be incapable of performance by substantially all persons other than designated individuals who possess said degree of skill;
 (b) generating an identity confirmed signal to satisfy a first necessary precondition for enabling the vehicle to be started in the event said identity confirming act is performed;
 (c) testing the alcohol content of a breath sample delivered by the prospective operator to determine the alcohol content of said sample;
 (d) generating a pass signal if said alcohol content is acceptable to satisfy a second necessary precondition for enabling the vehicle to be started; and
 (e) enabling the vehicle to be started when at least said first and second preconditions have been satisfied.

61. The method of claim 60 further comprising the step of:
 determining whether said breath sample corresponds to a deep lung sample of breath and, if so, generating a validity signal as a third necessary precondition for enabling the vehicle to be started.

62. The method of claim 60 wherein said identity confirming act requires blowing breath at the same physical location whereat the prospective operator must blow to deliver said breath sample.

63. The method of claim 61 wherein at least a portion of said identity confirming act is performed substantially contemporaneously with at least a portion of delivery of said bearth sample.

64. The method of claim 62 further comprising the step of determining whether said identity confirming act has been performed in fewer than a predetermined number of attempts regardless of whether any other preconditions for allowing the vehicle to start have been satisfied.

* * * * *

UNITED STATES PATENT AND TRADEMARK OFFICE
CERTIFICATE OF CORRECTION

PATENT NO. : 4,738,333

DATED : April 19, 1988

INVENTOR(S) : Donald W. Collier, Kip L. Fuller & Felix J.E. Comeau

It is certified that error appears in the above-identified patent and that said Letters Patent is hereby corrected as shown below:

At Col. 1, line 68, please delete "uper" and insert thereat --upper--.

At Col. 2, line 46, please delete "stated" and insert thereat --started--.

At Col. 4, line 56, please delete "smple" and insert thereat --sample--.

At Col. 4, line 61, please delete "value" and insert thereat --valid--.

At Col. 5, line 22, please delete "#812" and insert thereat --#813--.

At Col. 5, line 24, please delete "#813" and insert thereat --#812--.

At Col. 6, line 40, please delete "palcing" and insert thereat --placing--.

At Col. 6, line 43, please delete "is" and insert thereat --it--.

At Col. 6, line 53, please delete "flowing" and insert thereat --blowing--.

At Col. 7, line 5, please delete "of" and insert thereat --and--.

UNITED STATES PATENT AND TRADEMARK OFFICE
CERTIFICATE OF CORRECTION

PATENT NO. : 4,738,333

DATED : April 19, 1988

INVENTOR(S) : Donald W. Collier, Kip L. Fuller & Felix J.E. Comeau

It is certified that error appears in the above-identified patent and that said Letters Patent is hereby corrected as shown below:

At Col. 7, line 17, please delete "blow" and insert thereat --blows--.

At Col. 7, line 59, after the word act, please delete "the" and insert thereat --and--.

At Col. 9, line 17, please delete "no" and insert thereat --not--.

At Col. 10, line 49, please delete "grce" and insert thereat --grace--.

At Col. 10, line 56, please delete "successfully" and insert thereat --successful--.

At Col. 13, line 17, please delete "in" and insert thereat --In--.

At Col. 13, line 35, please delete "sued" and insert thereat --used--.

At Col. 14, line 40, after the word breath, please delete "a".

At Col. 19, line 53, please delete "fo" and insert thereat --of--.

UNITED STATES PATENT AND TRADEMARK OFFICE
CERTIFICATE OF CORRECTION

PATENT NO. : 4,738,333
DATED : April 19, 1988
INVENTOR(S) : Donald W. Collier, Kip L. Fuller & Felix J.E. Comeau It is certified that error appears in the above-identified patent and that said Letters Patent is hereby corrected as shown below:

At Col. 20, line 44, after the word attempts, please delete "a".

At Col. 22, line 68, please delete "connecting" and insert thereat --connectable--.

At Col. 23, line 23, please delete "whetehr" and insert thereat --whether--.

Signed and Sealed this

Fifth Day of September, 1989

Attest:

DONALD J. QUIGG

*Attesting Officer*

*Commissioner of Patents and Trademarks*